US005714493A

United States Patent [19]
Myers et al.

[11] Patent Number: 5,714,493
[45] Date of Patent: Feb. 3, 1998

[54] ARYL AND HETEROARYL QUINAZOLINE COMPOUNDS WHICH INHIBIT CSF-1R RECEPTOR TYROSINE KINASE

[75] Inventors: Michael R. Myers, Reading; Alfred P. Spada, Lansdale; Martin P. Maguire, Mont Clare; Paul E. Persons, King of Prussia; Asher Zilberstein, Broomall; Chin-Yi Jenny Hsu, West Chester; Susan E. Johnson, Upper Darby, all of Pa.

[73] Assignee: Rhone-Poulenc Rorer Pharmaceuticals, Inc., Collegeville, Pa.

[21] Appl. No.: 652,444

[22] PCT Filed: Dec. 8, 1994

[86] PCT No.: PCT/US94/14180

§ 371 Date: Jun. 4, 1996

§ 102(e) Date: Jun. 4, 1996

[87] PCT Pub. No.: WO95/15758

PCT Pub. Date: Jun. 15, 1995

Related U.S. Application Data

[63] Continuation-in-part of Ser. No. 229,886, Apr. 19, 1994, which is a continuation-in-part of Ser. No. 166,199, Dec. 10, 1993, Pat. No. 5,480,883, which is a continuation-in-part of Ser. No. 988,515, Dec. 10, 1992, abandoned, which is a continuation-in-part of Ser. No. 698,420, May 10, 1991, abandoned.

[51] Int. Cl.[6] .................................................. A61K 31/505
[52] U.S. Cl. .......................... 514/259; 514/252; 514/253; 514/254; 514/249; 514/248; 514/230.5
[58] Field of Search ................................ 514/259, 248, 514/249, 252, 253, 254, 230.5

[56] References Cited

U.S. PATENT DOCUMENTS

| 3,272,824 | 9/1966 | Ebetino et al. . |
| 3,715,358 | 2/1973 | Witzel et al. . |
| 3,718,743 | 2/1973 | Shen et al. . |
| 3,985,749 | 10/1976 | Foster . |
| 4,322,420 | 3/1982 | Kobyashi et al. . |
| 4,343,940 | 8/1982 | Kreighbaum et al. . |
| 4,464,375 | 8/1984 | Kobayashi et al. . |
| 4,465,686 | 8/1984 | Lesher et al. . |
| 4,599,423 | 7/1986 | Lesher et al. . |
| 4,661,499 | 4/1987 | Young et al. . |
| 5,134,148 | 7/1992 | Crawley et al. . |
| 5,457,105 | 10/1995 | Barker . |
| 5,580,870 | 12/1996 | Barker et al. . |

FOREIGN PATENT DOCUMENTS

| 9331010 | 7/1993 | Australia . |
| 0 520 722 | 12/1992 | European Pat. Off. . |
| 0 566 226 A1 | 10/1993 | European Pat. Off. . |
| 0 635 498 A1 | 1/1995 | European Pat. Off. . |
| 1543560 | 4/1979 | United Kingdom . |
| 92/20642 | 11/1992 | WIPO . |
| 95/23141 | 8/1995 | WIPO . |

OTHER PUBLICATIONS

Ried et al., 3-Phenyl-chinolin-7,8-diol, Beilstein-Band EIII/IV 21, p. 2436 (1952).
Takase et al., Preparation of N-containing heterocyclic compounds as phosphodiesterase inhibitors Chemical Abstracts, vol. 119:203427t, p. 898 (1993).
Budesinsky et al., Alkoxyquinazolines, Chemical Abstracts, Vo. 86:140078g, p. 569 (1977).
Barnish et al., Quinazoline derivatives, Chemical Abstracts, vol. 82:31349t, p. 503 (1975).
Marquis et al., Antithrombogenic quinazolines, Chemical Abstracts, vol. 77:70423d, p. 59 (1972).
Cronin et al., Hypotensive and bronchodilatory quinolines, isoquinolines, and quinazolines, Chemical Abstracts, vol. 70:68419, p. 397 (1969).
Takase et al., Cyclic GMP Phosphodiesterase Inhibityors. 2. Requirement of 6–Substitution of Quinazoline Derivatives for Potent and Selective Inhibitory Activity, J. Med. Chem., vol. 37, pp. 2106–2111 (1994).
Byford et al., o–Aminophenyl alkyl/aralkyl ketones and their derivativbes, Chemical Abstracts, vol. 111:39292g, p. 594 (1989).
Gopinathan et al., Ruthenium(II) complexes containing nitrogen heterocyclics, Chemical Abstracts, vol. 106:206623w, p. 704 (1987).
Lin et al., Studies on antiarrhythmics, Chemical Abstracts, vol. 96:122728w, p. 695 (1982).
Lederer et al., New synthesis of quazodine–type 7–methoxy–and 6,7–dimethoxyquinazolines, Chemicals Abstracts, vol. 84:105533p, p. 575 (1976).
Yoshina, Quinoline Derivatives, Chemical Abstract, vol. 84:164632t, p. 453 (1976).
Tamao et al., Nickel–Phosphine Complex–Catalyzed Grignard Coupling— II Grignard Coupling of Heterocyclic Compounds, Tetrahedron, vol. 38, No. 22, pp. 3347–3354 (1982).
Yamamoto et al., Studies on Organometallic Compounds. III. Reaction of Trimethylstannylazines with Acyl Chlorides. A Novel C–C Bond Formation of Pyridine Nuclei, Chem. Pharm. Bull., vol. 30, No. 6, pp. 2003–2010 (1982).
Saeed et al., Preparation of Phenylquinoxaline from alpha, alpha–Diaminoketones and Dimethyl–o–phenylenediamine, J.Heterocyclic Chem., vol. 20, pp. 1739–1740 (1983).
Ishikura et al., A Simple and Regioselective Preparation of 2–or 3–Substituted Quinoline Derivatives Via Dialkylquinolylboranes, Heterocycles, vol. 23, No. 9, pp. 2375–2386 (1985).

(List continued on next page.)

Primary Examiner—José G. Dees
Assistant Examiner—Mary C. Cebuilak
Attorney, Agent, or Firm—Raymond S. Parker, III; James A. Nicholson; Martin F. Savitzky

[57] ABSTRACT

This invention relates to the treatment of intimation in a patient suffering from such disorder. More specifically, the invention relates to mono- and/or bicyclic aryl or heteroaryl quinazoline compounds in the treatment of inflammation.

1 Claim, No Drawings

OTHER PUBLICATIONS

Barker et al., Dehalogenation of 1–Halothienyldi–and –Tetrahydroisoquinolines by Sodium Methoxide in Dimethyl Sulfoxide, Chemical Abstract, vol. 103:123929z, p. 709 (1985).

Yamamoto et al., General Method for Synthesis of Bipyridines: Palladium Catalyzed Cross–Coupling Reaction of Trimethylstannylpyridines with Bromopyridines, Synthesis, pp. 564–565 (Jul. 1986).

Epling et al., Sulfur–Containing 2–Arylquinolinemethanols as Potential Antimalarials, Chemical Abstract, vol. 108:55860j, p. 704 (1988).

Stern et al., Potential–Dependent Surface Chemistry of 3–Pyridinecarboxylic Acid (Niacin) and Related Compounds at Pt(111) Electrodes, J. Am. Chem. Soc., vol. 111, No. 3, pp. 877–891 (1989).

ARYL AND HETEROARYL QUINAZOLINE COMPOUNDS WHICH INHIBIT CSF-1R RECEPTOR TYROSINE KINASE

This application is a continuation-in-part application of U.S. Ser. No. 08/229,886, filed Apr. 19, 1994, which is a continuation-in-part of Ser. No. 08/166,199, filed Dec. 10, 1993, now U.S. Pat. No. 5,480,883, which is a continuation-in-part of Ser. No. 07/988,515, filed Dec. 10, 1992, now abandoned which is a continuation-in-part application of U.S. Ser. No. 07/698,420, filed May 10, 1991 and a continuation-in-part application of PCT International Application Ser. No. PCT/US92/03736, filed May 6, 1992, which has entered the U.S. National Stage as Ser. No. 08/146,072, filed Nov. 8, 1993.

BACKGROUND OF THE INVENTION

1. Field of the Invention

This invention relates to the modulation and/or inhibition of cell signaling, cell proliferation, the control of abnormal cell growth and cell inflammatory response. More specifically, this invention relates to the use of mono- and/or bicyclic aryl or heteroaryl quinazoline compounds which exhibit selective inhibition of differentiation, proliferation or mediator release by effectively inhibiting CSF-1R tyrosine kinase activity.

Normal cell growth is believed to be triggered by the exposure of the cellular substrate to one or more growth factors, examples of which are insulin, epidermal growth factor (EGF) and platelet-derived growth factor (PDGF). Receptors for such growth factor are imbedded in and penetrate through the cellular membrane. The initiation of cellular reproduction is believed to occur when a growth factor binds to the corresponding receptor on the external surface of the cellular membrane. This growth factor-receptor binding alters the chemical characteristics of that portion of the receptor which exists within the cell and which functions as an enzyme to catalyze phosphorylation of either an intracellular substrate or the receptor itself, the latter being referred to as autophosphorylation. Examples of such phosphorylating enzymes include tyrosine kinases, which catalyze phosphorylation of tyrosine amino acid residues of substrate proteins.

Many disease states are characterized by the uncontrolled growth of cells. These disease states involve a variety of cell types and include disorders such as cancer, leukemia, psoriasis, inflammatory diseases, bone diseases, atherosclerosis and restenosis occuring subsequent to angioplastic procedures. The inhibition of tyrosine kinases is believed to have utility in the control of deregulated cellular proliferation, i.e., cellular proliferative disorders.

Initiation of autophosphorylation, i.e., phosphorylation of the growth factor receptor itself, and of the phosphorylation of a host of intracellular substrates are some of the biochemical events which are involved in mediator release and cell proliferation.

REPORTED DEVELOPMENTS

Inhibitors of p56$^{lck}$ tyrosine kinase have been reported in the literature by Bolen, J. B. et al. FASEB J. 1992, 3403., Mustelin, T. et al. TIBS 1993,215.; Eichmann, K. *Angew. Chem. Int. Ed. Eng.* 1993, 54.; and Klausner, R. D. Samelson, L. E. *Cell* 1991, 875. These include compounds that are potent but nonselective inhibitors, such as staurosporine, which is competitive with ATP or compounds that are very weak tyrosine kinase inhibitors, but are somewhat selective, such as the flavonoid quercetin.

A series of dihydroxy-isoquinolines have been been reported by Burke, T. R. et al. (*Biorg. & Med. Chem. Lett.* 1992, 1771; J. Med. Chem. 1993 3010 and *J. Med. Chem.* 1993,3015) that have potent p56$^{lck}$ inhibiting activity. Potential therapeutic uses for selective inhibitors of p56$^{lck}$ include the treatment of autoimmune diseases such as rheumatoid arthritis or transplant rejection.

p56$^{lck}$, which is a non-receptor tyrosine kinase, has been shown to be important in intracellular signaling in T-cells. It is assumed that inhibitors of p56$^{lck}$ kinase activity perturb the activation of T-cells and therefore a selective inhibitor could prove useful in the treatment of T-cell mediated conditions such as organ rejection, rheumatoid arthritis or other auto-immune diseases.

SUMMARY OF THE INVENTION

The present invention describes compounds which are inhibitors of the colony stimulating factor-1 receptor tyrosine kinase, CSF-1R, activity and have activity in a p56$^{lck}$ cell-free assay. These compounds do not appear to have any significant serine/threonine kinase inhibitory activity and in addition, compounds within the scope of this invention do not demonstrate significant PDGF-R activity in a cell-free assay. Compounds of this invention are also weak inhibitors of PDGF-induced mitogenesis which may suggest that these compounds inhibit other src-like tyrosine kinases involved in the signal transduction pathway.

Compounds within the scope of this invention are inhibitors of the colony stimulating factor-1 receptor tyrosine kinase, CSF-1R, activity. A selective inhibitor of the tyrosine kinase activity of this receptor, which is closely related to the platelet-derived growth factor receptor (PDGF-R), has never been reported. Compounds of this invention are selective inhibitors of CSF-1R tyrosine kinase activity and are useful for elucidating the importance of CSF-1 and CSF-1 receptor signaling in bone remodeling and hematopoeisis. In addition compounds inhibiting growth factor-induced CSF and/or lck signalling are described herein.

In accordance with the present invention, there is provided pharmaceutical compositions for inhibiting abnormal cell proliferation and/or differentiation or mediator release in a patient suffering from a disorder characterized by such proliferation activity, comprising the administration to a patient a tyrosine kinase composition which effectively inhibits CSF-1R tyrosine kinase activity in a CSF-1R inhibiting effective amount of a mono- aryl or hetero-aryl quinazoline compound exhibiting inhibition of differentiation, proliferation or mediator release activity wherein each aryl group is a ring system containing 0–4 hetero atoms, said compound being optionally substituted or polysubstituted.

Another aspect of the present invention relates to a method of inhibiting abnormal cell proliferation and/or differentiation or mediator release comprising, in admixture with a pharmaceutically acceptable carrier, a pharmaceutically effective amount of a compound of the aforementioned type. Another aspect of this invention comprises compounds useful in the practice of the present method.

With respect to the aspects of this invention, the compounds described by Formula I below constitute a class of the aforementioned mono- and bicyclic aryl or heteroaryl quinazoline compounds for use in the practice of the present invention:

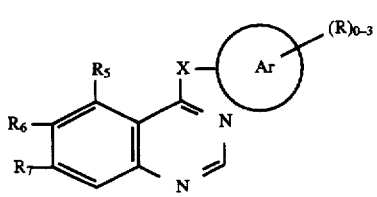

Formula I wherein

Ar is a substituted or unsubstituted mono- or bi-cyclic aryl or heteroaryl ring system of about 5 to about 12 atoms and where each monocyclic ring may contain 0 to about 3 hetero atoms, and each bicyclic ring may contain 0 to about 4 hetero atoms selected from N, O and S provided said hetero atoms are not vicinal oxygen and/or sulfur atoms and where the substituents may be located at any appropriate position of the ring system and are described by R.;

X is a bond, O, S, SO, $SO_2$, $OCH_2$, C=C, C≡C, C=S, $SCH_2$, NH, $NHCH_2$, $NR_4$ or $NR_4CH_2$;

R independently includes hydrogen, alkyl, alkenyl, phenyl, aralkyl, aralkenyl, hydroxy, hydroxyalkyl, alkoxy, alkoxyalkyl, aralkoxy, aryloxy, acyloxy, halo, haloalkyl, nitro, cyano, amino, mono- and di-alkylamino, acylamino, carboxy, carboxyalkyl, carbalkoxy, carbaralkoxy, carbalkoxyalkyl, carbalkoxyalkenyl, aminoalkoxy, amido, mono- and di-alkylamido and N,N-cycloalkylamido, alkylthio, alkylsulfinyl, sulfonyl, mono- and di-alkyl sulfonyl, sulfamoyl, mono- and di- alkyl sulfamoyl, halophenyl or benzoyl; and R and R together may also form a ketone group.

$R_4$ is alkyl, $-CH_2-CH_2-$ or $-CH_2-CH_2-CH_2-$; and $R_5$, $R_6$ and $R_7$ are independently hydrogen, alkyl, alkylthio, cycloalkyl, hydroxy, alkoxy, aralkoxy, aryl, halo, haloalkyl, carboxy or carbalkoxy; or a pharmaceutically acceptable salt thereof.

Preferred Ar monocyclic aryl or heteroaryl rings include substituted or unsubstituted benzene, pyrrole, thiophene, furan, thiazole, imidazole, pyrazole, 1,2,4-triazole, pyridine, 2(1H)-pyridone, 4(1H)-pyridone, pyrazine, pyrimidine, pyridazine, isothiazole, isoxazole, oxazole and tetrazole.

Preferred Ar bicyclic aryl or heteroaryl rings include substituted and unsubstituted naphthalene, tetralin, naphthyridine, benzofuran, benzothiophene, indole, 2,3-dihydroindole, 1H-indazole, indoline, benzopyrazole, 1,3-benzodioxole, benzoxazole, purine, coumarin, chromone, quinoline, tetrahydroquinoline, isoquinoline, benzimidazole, quinazoline, pyrido[2,3-b]pyrazine, pyrido[3,4-b]pyrazine, pyrido[3,2-c]pyridazine, pyrido[3,4-b]-pyridine, 1H- pyrazole[3,4-d]pyrimidine, pteridine, 2(1H)-quinolone, 1(2H)-isoquinolone, 1,4-benzisoxazine, benzothiazole, quinoxaline, quinoline-N-oxide, isoquinoline-N-oxide, quinoxaline-N-oxide, quinazoline-N-oxide, benzoxazine, phthalazine, or cinnoline.

More preferred Ar rings include substituted and unsubstituted benzene, pyridine, thiophene, naphthalene, quinoline, indole and 1H- pyrazole[3,4-d]-pyrimidine.

Preferred R substituents include hydrogen, alkyl, alkenyl, hydroxy, alkoxy, halo, haloalkyl, amino, mono-and di-alkylamino, acylamino, carboxy, carbalkoxy, amido, mono- and di-alkylamido, N,N-cycloalkylamido, alkylthio, alkylsulfinyl, alkylsulfonyl or sulfamoyl, alkyl, alkenyl, phenyl, aralkyl, aralkenyl, and R may also form a keto group.

As employed above and throughout this disclosure, the following terms, unless otherwise indicated, shall be understood to have the following meanings:

"Monocyclic aryl or heteroaryl" means a carbocyclic or heterocyclic aromatic ring. Preferred rings include phenyl, thienyl, pyridyl, 2(1H)-pyridonyl, 4(1H)-pyridonyl, furyl, pyrimidinyl, imidazolyl, thiazolyl, oxazolyl and tetrazolyl.

"Bicyclic aryl or heteroaryl" means a bicyclic ring system composed of two fused carbocyclic and/or heterocyclic aromatic rings. Preferred rings include naphthyl, indolyl, benzothienyl, benzofuranyl, quinolinyl, chromonyl, 1(2H)-isoquinolonyl, isoquinolinyl, benzimidazolyl, benzothiazolyl, quinoxalinyl, naphthyridinyl, cinnolinyl, phthalazinyl, pyrido[2,3-b]pyrazinyl, pyrido[3,4-b] pyrazinyl, pyrido[3,2-c]pyridazinyl, pyrido[3,4-b]-pyridinyl, pteridinyl, and quinazolinyl.

"Alkyl" means a saturated aliphatic hydrocarbon, either branched- or straight-chained. Preferred alkyl is "lower-alkyl" having about 1 to about 6 carbon atoms. Examples of alkyl include methyl, ethyl, n-propyl, isopropyl, butyl, sec-butyl, t-butyl, amyl and hexyl.

"Cycloalkyl" means a cyclic aliphatic group comprising from about three to about seven carbon atoms. Preferred cycloalkyl groups include cyclopropyl, cyclobutyl, cyclohexyl and cycloheptyl.

"Alkoxy" refers to an alkyl-O-group. Preferred alkoxy groups include methoxy, ethoxy, propoxy and butoxy.

"Aryloxy" refers to an aryl-O-group. The preferred aryloxy group is phenoxy.

"Aralkyl" means an alkyl group substituted by an aryl radical. The preferred aralkyl groups are benzyl or phenethyl.

The preferred aralkoxy groups are benzyloxy and phenethoxy.

The preferred acyloxy groups are acetoxy and benzyloxy;

"Halo" means halogen. Preferred halogens include chloride, bromide and fluoride.

The preferred haloalkyl groups are mono-, di- and trifluoromethyl.

The more preferred compounds of this invention include those compounds of Formula I where Ar is phenyl or naphthyl;

R is hydrogen, alkyl, alkoxy, hydroxy, halo or trifluoromethyl.

X is a bond, NH or $NR_4$; and $R_5$, $R_6$ and $R_7$ are independently hydrogen or alkoxy.

The most preferred compounds are those described where

Ar is phenyl;

X is NH or NMe; and $R_5$, $R_6$ and $R_7$ are independently hydrogen or methoxy.

It is intended that N-oxides of the above described aminoquinazolines are encompassed within the scope of this invention.

Special embodiments of this invention inhibiting the growth factor or tyrosine kinase include the following:

A. Compounds of Formula I where:

X is a bond, $NR_4$, S or O, the inhibiting cell proliferation and/or differentiation or mediator release is especially characterized by CSF-1 activity.

B. Compounds of Formula I where:

X is a bond, NH, S or O, the inhibiting cell proliferation and/or differentiation or mediator release is especially characterized by Ick/EGF activity.

C. Compounds of Formula I where:

X is a bond and Ar is phenyl, indolyl, pyrrolyl, thienyl, pyridyl, naphthyl, a bicyclic aryl, a bicyclic heteroaryl or substituted phenyl, indolyl, pyrrolyl, thienyl, pyridyl, naphthyl, bicyclic aryl, bicyclic heteroaryl, the inhibiting cell proliferation and/or differentiation or mediator release is especially characterized by Ick activity.

D. Compounds of Formula I where:

X is NH, $R_6$ and $R_7$ are alkoxy and Ar is phenyl having at least one substituent in the 3, 4 and / or 5 positions of hydroxy or alkoxy, the inhibiting cell proliferation and/or differentiation or mediator release is especially characterized by Ick activity.

The compounds of this invention may be useful in the form of the free base, in the form of salts and as a hydrate.

In general the compounds useful for the method of inhibiting cell proliferation and/or differentiation or mediator release may be prepared by the coupling reaction of a palladium catalyzed aryl or heteroarylstannane with an aryl or heteroarylhalide or triflate.

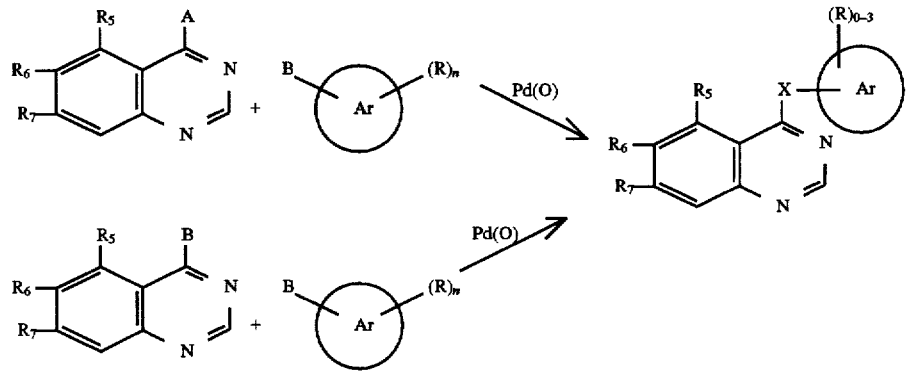

All forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope Of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

The corresponding acid addition salts comprise the following: hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may be prepared by employing procedures known in the literature starting from known compounds or readily prepared intermediates. Exemplary general procedures follow.

where A is halogen or triflate and B is trialkylstannane and R is as previously described.

The 4-haloquinazoline starting materials are prepared in the classical way using anthranilic acid derivatives and formamide at reflux to provide the intermediate quinazolinones. Subsequent treatment with $POCl_3$ at about 110° C. for about two hours provides the chloroquinazolines. The final products are prepared via a condensation with the appropriate aniline derivative in a polar solvent such as ethanol. In the case of the phenoxy or thiophenoxy derivatives, the metal salt (preferably Na) is prepared and refluxed for several hours with the appropriate haloquinazoline in a solvent such as THF.

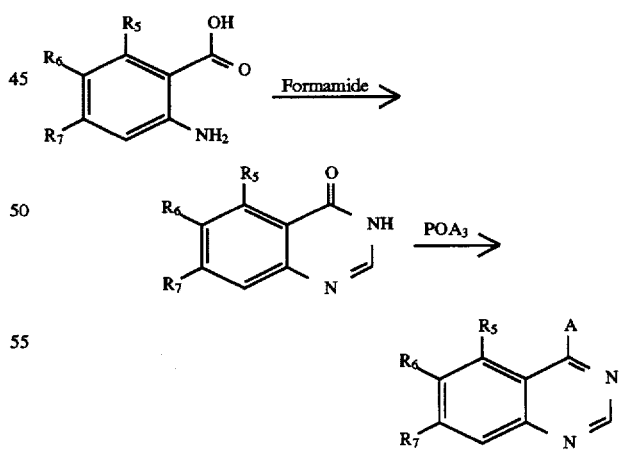

The aryl and heteroarylstannanes may be prepared from the corresponding halide (preferably bromide or iodide) by conversion to the aryllithium by reaction with t-butyllithium at decreased temperatures, preferably about −78° C. followed by reaction with a halotrialkylstannane.

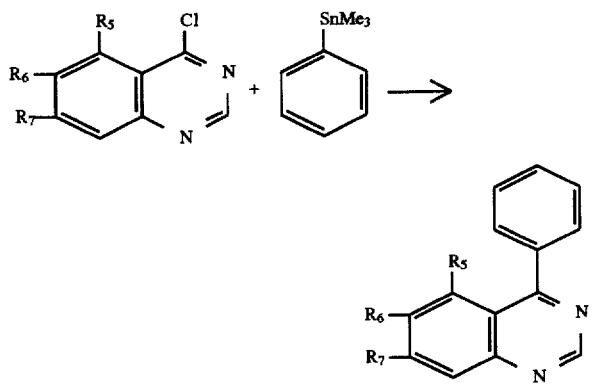

Of course these products may also be prepared in the reverse manner using the aryl or heteroarylhalides with the the corresponding stannane.

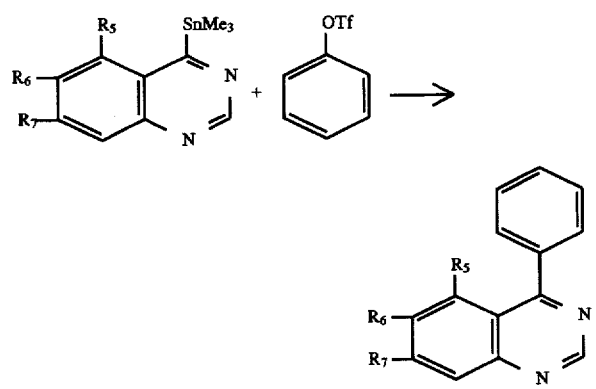

The quinazoline stannanes intermediates may be prepared by the action of trimethyltin sodium on aryl halides as described in Chem. Pharm. Bull. 1982, 30, 1731–1737:

The preparation of the compounds useful in this invention are described in Applicants' copending applications U.S. Ser. No. 08/166,199, filed Dec. 10, 1993 and U.S. Ser. No. 08/229,886, filed Apr. 19, 1994 of which this application claims priority. U.S. Ser. No. 08/166,199 and U.S. Ser. No. 08/229,886 are hereby incorporated herein by reference.

Further, the following examples are representative of the processes used to synthesis the compounds of this invention.

The below examples and those described in U.S. Ser. No. 08/166,199 may be followed to prepare any of the desired compounds of this invention. A representative list of compounds which may be prepared is shown below.

EXAMPLE 1

4-(3-chlorophenoxy)-6,7-dimethoxyquinazoline

THF (5 ml) and NaH (60% disp in oil, approx. 28 mg) is added to a dry flask maintained under inert atmosphere at room temperature. 3-Chlorophenol (0.09 g) is added as a soln. in THF (1 mL) and stirring is continued until the solution became clear. 4-Chloro-6,7-dimethoxyquinazoline is added all at once (as the solid) and stirring was maintained overnight at RT. The solution is partitioned between $CH_2Cl_2$ and 5% NaOH. The organic layer is washed with brine, dried ($Na_2SO_4$) and concentrated. Flash column chromatography (40% EtOAc/Hex) provided the pure compound. An analytical sample is obtained by recrystallization from EtOAc/Hex to provide 4-(3-chlorophenoxy)-6,7-dimethoxyquinazoline (0.05 g), white needles, m.p. 152°–153° C.

EXAMPLE 2

4-(1-methylsulphonylindol-3-yl)-6,7-dimethoxyquinazoline

Step A

N-methylsulfonyl-3-trimethylstannylindole

A solution of 5 g (15.57 mmol) of N-methylsulfonyl-3-iodoindole (5.1 g; 15.57 mmol) of hexamethylditin and 0.89 g (0.78 mmol) of Pd $(PPh3)_4$ in 75 mL of dry toluene is flushed thoroughly with nitrogen and heated to 90° C. for 4 hours. The mixture is then evaporated and chromatographed on silica gel (eluting with hexane and then with 10% ethyl acetate/hexane to give N-methylsulfonyl-3-trimethylstannylindole which is used directly in the next step.

Step B 4-(1-methylsulphonylindol-3-yl)-6,7-dimethoxyquinazoline

A solution of 1.33 g (4.01 mmol) of N-methylsulfonyl-3-trimethyl-stannylindole, 750 mg (3.34 mmol) of 4-chloro-6,7-dimethoxyquinazoline and 0.19 g (5 mol % 0.16 mmol) of Pd $(PPh_3)_4$ in 10 ml of dry dimethylformamide is flushed thoroughly with nitrogen and heated to 90° C. for 12 hours. The reaction mixture is diluted with methylene chloride washed with 10% ammonium hydroxide and stirred vigorously and then washed with water and the combined organics are washed with brine (75 mL), dried ($MgSO_4$) and evaporated to dryness. Recrystallization from ethyl acetate yields 4-(1-methylsulphonylindol-3-yl)-6,7-dimethoxyquinazoline (m.p. >220° C.).

The above examples may be followed to prepare any of the desired compounds of this invention. A representative list of compounds which may be prepared are shown below.

6,7-dimethoxy-4-naphthalen-2-ylethynylquinazoline, m.p. 158°–161° C.

4-(4-hydroxyphenyl)-6,7-dimethoxyquinazolinehydrochloride, m.p. >270° C. (dec)

4-(naphthalen-1-yl)-6,7-dimethoxyquinazoline, m.p. 144°–147° C.

4-(naphthalen-2-yl)-6,7-dimethoxyquinazoline, m.p. 115°–118° C.

4-phenylacetylenyl-6,7-dimethoxyquinazoline, m.p. 146°–148° C.

4-(3-fluoro-4-methoxyphenyl)-6,7-dimethoxyquinazoline, m.p. 207°–210° C.

4-(3-phenylphenyl)-6,7-dimethoxyquinazoline, m.p. 160°–163° C.

4-(2-phenylethylenyl)-6,7-dimethoxyquinazoline, m.p. 168°–169° C.

4-(2-methoxypyridin-5-yl)-6,7-dimethoxyquinazoline, m.p. 175°–176° C.

4-(1-benzylindol-3-yl)-6,7-dimethoxyquinazoline, m.p. 148°–150° C.

4-(indol-3-yl)-6,7-dimethoxyquinazoline, m.p. >240° C. (dec)

4-(1-methylindol-3-yl)-6,7-dimethoxyquinazoline hydrochloride, m.p. >230° C. (dec)

4-(1-methylsulphonylindol-3-yl)-6,7-dimethoxyquinazoline, m.p. >220° C. (dec)

4-(4-phenylpiperidin-1-yl)-6,7-dimethoxyquinazoline, m.p. 150°–151° C.

4-[4-(3-chlorophenyl)piperazin-1-yl]-6,7-dimethoxyquinazoline, m.p. 155°–156° C.

4-(N-methyl-3,4,5-trimethoxyanilino)-6,7-dimethoxyquinazoline, m.p. 149°–151° C.

(+−)-4-(2-methyl-1,2,3,4-tetrahydroquinolin-1-yl)-6,7-dimethoxyquinazoline hydrochloride, m.p. 198°–201° C. (dec)

4-(1,2,3,4-tetrahydroquinolin-1-yl)-6,7-dimethoxyquinazoline hydrochloride, m.p. 195°–197° C. (dec)

4-(N-methyl-4-methoxyanilino)-6,7-dimethoxyquinazoline hydrochloride, m.p. 202°–205° C.

4-(N-methyl-4-chloroanilino)-6,7-dimethoxyquinazoline hydrochloride, m.p. 220°–222° C.

4-(2,3-dihydroindol-1-yl)-6,7-dimethoxyquinazoline hydrochloride, m.p. 226°–229° C. (dec)

N-(6,7-dimethoxyquinazolin-4-yl)-N-methyl-N-(3-trifluoromethylphenyl)amine hydrochloride, m.p. 240°–243° C.

N-(3-chlorophenyl)-N-(6,7-dimethoxyquinazolin-4-yl)-N-methylamine hydrochloride, m.p. 235°–237° C.

N-(3-chlorophenyl)-N-(quinazolin-4-yl)-N-methyl-amine hydrochloride, m.p. 233°–235° C.

6,7-dimethoxy-4-naphthalen-1-yl-ethynylquinazoline, m.p. 175°–177° C.

4-(thien-3-yl)-6,7-dimethoxyquinazoline, m.p. 148.5°–151.5° C.

4-benzyl-6,7-dimethoxyquinazoline, m.p. 122.5°–125° C.

(6,7-dimethoxyquinazolin-4-yl)-5-indazolylamine hydrochloride, m.p. 261°–263° C. (dec)

N-(6,7-dimethoxyquinazolin-4-yl)-N-phenyl-N-ethylamine hydrochloride, m.p. 227°–230° C. (dec)

N-benzyl-N-(6,7-dimethoxyquinazolin-4-yl)-N-phenylamine hydrochloride, m.p. 269°–271° C.

N-(6-chloroquinazolin-4-yl)-N-methyl-N-phenylamine, m.p. 106°–108° C.

N-(3-chloro-phenyl)-N-(6,7-dimethoxyquinazolin-4-yl)-N-ethylamine hydrochloride, m.p. 261°–263° C.

N-(6,7-dimethoxyquinazolin-4-yl)-N-methyl-N-p-tolylamine hydrochloride, m.p. 230°–234° C. (dec)

N-benzyl-N-(6,7-dimethoxyquinazolin-4-yl)amine, m.p. 220°–225° C.

N-(4-methoxybenzyl)-N-(6,7-dimethoxyquinazolin-4-yl)amine, m.p. 194°–198° C.

N-(3,5-dimethoxybenzyl)-N-(6,7-dimethoxyquinazolin-4-yl)amine hydrochloride, m.p. 265°–269° C.

4-(3,4,5-trimethoxyphenoxy)-6,7-dimethoxyquinazoline, m.p. 228°–232° C.

N-(quinazolin-4-yl)-N-phenyl-N-methylamine hydrochloride, m.p. 242°–246° C. (dec)

N-(6,7-dimethoxyquinazolin-4-yl)-N-(4-morpholin-4-ylphenyl)amine hydrochloride, m.p. 231°–235° C. (dec)

4-(3-methoxythiophenoxy)-6,7-dimethoxyquinazoline, m.p. 139.5°–141.5° C.

4-[N-(5-indanyl)amino]-6,7-dimethoxyquinazoline hydrochloride, m.p. 244°–246° C. (dec)

4-(3-chlorothiophenoxy)-6,7-dimethoxyquinazoline, m.p. 152°–153.5° C.

4-(3-aminopyrazolyl)-6,7-dimethoxyquinazoline hydrochloride, m.p. 262°–264° C. (dec)

4-(1,4-benzodioxan-6-ylamino)-6,7-dimethoxyquinazoline hydrochloride, m.p. 267°–269° C. (dec)

6,7-dimethoxy-4-(α-naphthylamino)quinazoline hydrochloride, m.p. >250° C.

6,7-dimethoxy-4-(β-naphthylamino)quinazoline hydrochloride, m.p. >250° C.

4-(cyclohexylanilino)-6,7-dimethoxyquinazoline, m.p. 239°–244° C.

4-(3,4,5-trimethoxyanilino)-6,7-dimethoxyquinazoline hydrochloride, m.p. 260°–265° C.

6,7-dimethoxy-4-(N-methylanilino)quinazoline hydrochloride, m.p. >230° C.

4-(3-chlorophenoxy)-6,7-dimethoxyquinazoline, m.p. 152°–153° C.

6,7-dimethoxy-4-(1-naphthylthio)-quinazoline, m.p. 174.5–176.5° C.

6,7-dimethoxy-4-(2-naphthylthio)-quinazoline, m.p. 178°–179° C.

6,7-dimethoxy-4-(1-naphthyloxy)-quinazoline, m.p. 214°–215.5° C.

6,7-dimethoxy-4-(2-naphthyloxy)-quinazoline, m.p. 169°–170° C.

N-(6,7-dimethoxy-quinolazolin-4-yl)-N-(naphth-2-yl)-N-ethylamine hydrochloride, m.p. 236°–239° C. (dec)

6,7-dimethoxy-4-(naphthalene-2-sulfinyl)quinazoline, m.p. 182.5°–185° C.

6,7-dimethoxy-4-(naphthalene-2-sulfonyl)quinazoline 4-(3-chloroanilino)-6,7-dimethylquinazoline hydrochloride, m.p. 271°–274° C.

4-(3,5-dimethylanilino)-6,7-dimethylquinazoline hydrochloride, m.p. >275° C.

4-(N-methyl-4-methylanilino)-6,7-dimethylquinazoline hydrochloride, m.p. 235°–238° C.

6,7-dimethyl-4-(1-naphthylamino)quinazoline hydrochloride, m.p. 244°–247° C.

6,7-dimethyl-4-(7-trifluoromethyl-3,4-dihydro-2H-quinolin-1-yl)quinazoline hydrochloride, m.p. 240° C.

4-(N-methyl-3-methylanilino)-6,7-dimethylquinazoline hydrochloride, m.p. 205°–207° C.

4-(3-chlorophenylthio)-6,7-dimethylquinazoline hydrochloride, m.p. 197°–202° C.

4-(1-naphthylthio)-6,7-dimethylquinazoline hydrochloride, m.p. 204°–209° C.

4-(3,4-dimethoxyphenylthio)quinazoline, m.p. 115°–117° C.

PREPARATION OF PHARMACEUTICAL COMPOSITIONS AND PHARMACOLOGICAL TEST SECTION

Compounds within the scope of this invention exhibit significant activity as protein tyrosine kinase inhibitors and possess therapeutic value as cellular antiproliferative agents for the treatment of certain conditions including psoriasis, atherosclerosis and restenosis injuries. Further, specific inhibitors of CSF-1R tyrosine kinase activity are useful for elucidating the importance of CSF-1 and CSF-1 receptor signaling in bone remodeling and hematopoeisis. Compounds within the scope of the present invention exhibit the modulation and/or inhibition of cell signaling, cell proliferation, cell inflammatory response, the control of abnormal cell growth and can be used in preventing or delaying the occurrence or reoccurrence of such conditions or otherwise treating the condition.

To determine the effectiveness of compounds of this invention, the pharmacological tests described below, which are accepted in the art and recognized to correlate with pharmacological activity in mammals, are utilized. Compounds within the scope of this invention have been subjected to these various tests, and the results obtained are believed to correlate to useful cellular differentiation mediator activity. The below described tests are useful in determining the inhibition of the colony stimulating factor-1 receptor tyrosine kinase (CSF-1R) activity. The ability to inhibit the p561$^{lck}$tyrosine kinase activity of compounds disclosed herein is described. The results of these tests are believed to provide sufficient information to persons skilled in the pharmacological and medicinal chemistry arts to determine the parameters for using the studied compounds in one or more of the therapies described herein.

EGF-Receptor Purification

EGF-receptor purification is based on the procedure of Yarden and Schlessinger. A431 cells are grown in 80 cm$^2$ bottles to confluency ($2\times10^7$ cells per bottle). The cells are washed twice with PBS and harvested with PBS containing 11.0 mmol EDTA (1 hour at 37° C., and centrifuged at 600 g for 10 minutes. The cells are solubilized in 1 ml per $2\times10^7$ cells of cold solubilization buffer (50 mmol Hepes buffer, pH 7.6, 1% Triton X-100, 150 mmol NaCl, 5 mmol EGTA, 1 mmol PMSF, 50 µg/ml aprotinin, 25 mmol benzamidine, 5 µg/ml leupigptic, and 10 µg/ml soybean trypsin inhibitor) for 20 minutes at 4° C. After centrifugation at 100,000 g for 30 minutes, the supernatant is loaded onto a WGA-agarose column (100 µl of packed resin per $2\times10^7$ cells) and shaken for 2 hours at 4° C. The unabsorbed material is removed and the resin washed twice with HTN buffer (50 mmol Hepes, pH 7.6, 0.1% Triton X-100, 150 mmol NaCl), twice with HTN buffer containing 1M NaCl, and twice with HTNG buffer (50 mmol Hepes, pH 7.6, 0.1% Triton X-100, 150 mmol NaCl, and 10% glycerol). The EGF receptor is eluted batchwise with HTNG buffer containing 0.5M N-acetyl-D-glucosamine (200 µl per $2\times10^7$ cells.). The eluted material is stored in aliquots at −70° C. and diluted before use with TMTNG buffer (50 mmol Tris-Mes buffer, pH 7.6, 0.1% Triton X-100, 150 mmol NaCl, 10% glycerol).

ATP and EGF Dependence of Autophosphorylation

WGA-purified EGF receptor from A431 cells (0.5 µg/assay is activated with EGF (0.85 µM) for 20 minutes at 4° C. The assay is performed at 15° C. and initiated by addition of $Mg(Ac)_2$ (60 mmol), Tris-Mes buffer, pH 7.6 (50 mmol), $[^{32}P]$ATP (carrier free, 5 µCi/assay), and increasing concentrations of nonradioactive ATP. The assay is terminated after 10-sec by addition of SDS sample buffer. The samples are run on a 6% SDS polyacrylamide gel. The gel is dried and autoradiographed as described above. The relevant radioactive bands are cut and counted in the Cerenkov mode. The $K_m$ for ATP determined in this fashion is found to be 7.2 µM. With use of the 10-sec assay protocol, the EGF concentration dependence of EGF-RK autophosphorylation is determined.

Inhibition of EGF-R Autophosphorylation

A431 cells are grown to confluence on human fibronectin coated tissue culture dishes. After washing 2 times with ice-cold PBS, cells are lysed by the addition of 500 µl/dish of lysis buffer (50 mmol Hepes, pH 7.5, 150 mmol NaCl, 1.5 mmol $MgCl_2$, 1 mmol EGTA, 10% glycerol, 1% triton X-100, 1 mmol PMSF, 1 mg/ml aprotinin, 1 mg/ml leupeptin) and incubating 5 minutes at 4° C. After EGF stimulation (500 µg/ml 10 minutes at 37° C.)immunoprecipitation is performed with anti EGF-R (Ab 108) and the autophosphorylation reaction (50 µl aliquots, 3 µCi $[\gamma$-$^{32}P]$ATP) sample is carried out in the presence of 2 or 10 µM of compound of the present invention, for 2 minutes at 4° C. The reaction is stopped by adding hot electrophoresis sample buffer. SDA-PAGE analysis (7.5% els) is followed by autoradiography and the reaction is quantitated by densitometry scanning of the x-ray films.

Cell Culture

Cells termed HER 14 and K721A (=DK) are prepared by transfecting NIH3T3 cells (clone 2.2) (From C. Fryling, NCI, NIH), which lack endogenous EGF-receptors, with cDNA constructs of wild-type EGF-receptor or mutant EGF-receptor lacking tyrosine kinase activity (in which Lys 721 at the ATP-binding site is replace by an Ala residue, respectively). All cells are grown in DMEM with 10% calf serum (Hyclone, Logan, Utah).

Further tests which show the effectiveness and selectivity of compounds of this invention to inhibit cell proliferation and/or differentiation or mediator release are as follows.

CSF-1R Cell-free Autophosphorylation Assay

For a regular 28 tube assay (14 samples per 15 well gel):
In 2 ml eppendorf tube: 140 mg protein A sepharose (5 mg/sample)

Swell in 20 mM Hepes pH 7.5 and wash 2x in Hepes
Add 280 λα-CSF-1R
20 min RT shaking

| | |
|---|---|
| Wash 3x in HNTG pH 7.5: | 20 mM Hepes |
| | 150 mM NaCl |
| | 0.1% triton X-100 |
| | 10% glycerol |
| In 15 ml tube: 2.8 ml lysate lysis buffer: | |
| | 20 mM Hepes |
| | 1.5 mM $MgCl_2$ |
| | 150 mM NaCl |
| | 1 mM EGTA |
| | 10% glycerol |
| | 1% triton X-100 |

Protease inhibitors added fresh:
PMSF: 8 mg/ml=2500x in 100% ETCH, store frozen, add 100 λ/10 ml lysis buffer
Aprotinin: 10 mg/ml=250x in $H_2O$, store frozen, add 40 λ/10 ml lysis buffer
Leupeptin: 1 mg/ml=250x in H20, store frozen, add 40 λ/10 ml lysis buffer
Add washed beads to stimulated lysate and incubate 90 min 4° C. on rotator or shaking
prepare 28 compound tubes:
make 40 mM solutions of compounds in 100% DMSO
make serial dilutions in 50 mM Tris pH 7.5+10 mM $MnCl_2$
aliquot 10λ compound solution into each 1 ml eppendorf reaction tube waiting on ice, control blanks get 10% buffer
Wash beads 1x HNTG, 2x 10mM Tris pH 7.5

| | |
|---|---|
| Add 10λ ATP solution: | 312λ 50 mM Tris pH 7.5 + 10 mM $MnCl_2$ |
| | 2.7λ cold ATP (stock of 10 mM in 50 mM Tris = 20 µM final) |
| | 35l$^{32}$P-ATP (10µ Ci/sample) |

Vortex, incubate 10 min on ice
Add 45λ 2x SDS-sample buffer, heat 95° C. 6 min
7.5% SDS-PAGE, fix, dry, expose (usually 4 hrs)
Ick Kinase: Immunoprecipitated from Jurkat lysate A. Jurkat cells (human T-cell leukemia, ATCC clone #E6-1) are grown in suspension in RPMI 1640 medium with 10% fetal calf serum, 100 U/ml penicillin/streptomycin, and 2 mM L-glutamine in a 37° C. incubator at 5% $CO_2$.

B. Cells are grown to $1-1.5\times10^6$ cells/ml media, pelleted by centrifugation, and lysed in lysis buffer at $10^8$ cells/ml buffer (50 mM tris (pH 8), 150 mM NaCl, 5 mM EDTA, 10% glycerol, and 1% NP-40, to which fresh protease and phosphatase inhibitors are added as described above for A431 lysate). Lysates stored at −70° C.

C. Immunoprecipitation: 3–4 mg Protein-A sepharose/ sample washed 2x 20 mM Hepes (pH 7.5). 1 ul α-lck antibody (prepared as polyclonals in rabbits using a peptide antigen corresponding to the N-terminal region of human Ick) per sample added to the Protein-A and shaken 20 min at room temperature. After washing 3X HNTG, lysate from $2\times10^6$ cells is added to each sample, rotated 2 hr at 4° C., then washed 3x HNTG (2nd wash containing 0.5N NaCl). If all samples contain identical concentrations of the enzyme, then the immuno-precipitation can be done in bulk and alloquoted to appropriate numbers of tubes prior to assay set-up.

D. Compound screening in the cell-free Ick kinase assay: Compounds (40 mM stocks in DMSO) are initially screened at concentrations of 10 and 100 uM in samples containing Ick immuno-precipitated from $2\times10^6$ cells, 5 uM cdc2 (a p34^cdc2-derived synthetic peptide (N6–20) prepared by R. Howk, RPR)[7], 5 mM $MnCl_2$, 5 uM ATP and 30 uCi g$^{32}$P-ATP (6000 Ci/mmol, NEN) in 20 mM hepes (pH 7.5) for 5 min at 30° C. Samples are analyzed by 5–15% SDS-PAGE and autoradiography as described for EGFR kinase assays.

E. Intact cell activation/inhibition studies:~5×10$^7$ cells per sample in 1 ml media are activated with either 10 ug a-CD3 (clone Cris 7, Biodesign) for 1 min at 37° C. or 20 ng PMA and 10 ug PHA for 20 min at 37° C. in the presence and absence of compound (added earlier so that the total time of compound incubation is 30 min). Incubations are terminated by centrifugation and lysis (as described). Samples are analyzed by immunoprecipitation (aPY (100 ul/10$^8$ cells), a-PLC (100 ul/10$^8$ cells), or a-zeta (20 ul/10$^8$ cells)), followed by SDS-PAGE and western blotting onto nitrocellulose and immunoblotting using RC20 recombinant aPY-HRP Transduction Labs) and ECL (Amersham).

cAMP-dependent Protein Kinase (PKA) Assay

Selectivity assay for compounds is performed as follows. Each sample contains 0.4 pmolar units PKA (from rabbit muscle, Sigma), 1 uM cAMP, 50 uM Tris-HCL (pH7), 10 mM MgAc, 50 ug BSA, 16 uM Kemptide substrate (specific cAMP kinase phosphate acceptor whose sequence corresponds to the pig liver pyruvate kinase phosphorlyation site), 16 uM ATP, 16 uCi $^{32}$P-ATP (6000 Ci/mmol, NEN), +/− compound and $dH_2O$ to a final volume of 200 ul. Reactions proceed for 5 min. at 30° C., and are terminated by the addition of 100 ul 375 mM $H_3PO_4$. 50 ul each sample spotted onto Whatman P81 phosphocellulose filters, which are washed 3X (15 min.) in 75 mM $H_3PO_4$, followed by an acetone rinse and dry (Cerenkov) counting.

In view of the results of the above test, compounds of the present invention can be shown to be selective.

The following tables show examples of representative compounds of this invention and their test results as determined by the above inhibition of CSR-1R and Ick procedures.

| Structure | Ick activity IC$_{50}$ (μM) | CSF-R activity IC$_{50}$ (μM) |
|---|---|---|
| 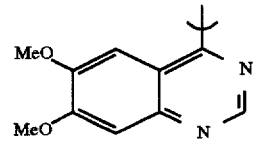 | | |
| 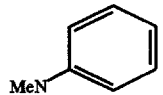 | >10 | 6 |
| 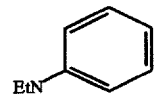 | 100 | 7 |
| 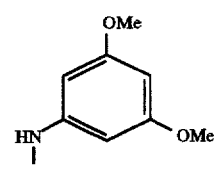 | >50 | 0.18 |

-continued

| Structure | Ick activity IC$_{50}$ (μM) | CSF-R activity IC$_{50}$ (μM) |
|---|---|---|
| 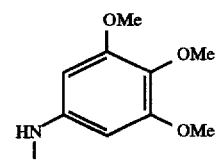 | | |
| 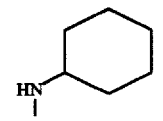 | >50 | 0.5 |
| 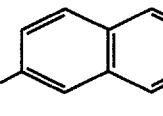 | >50 | 4.0 |
| 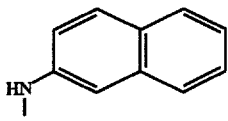 | 10 | >100 |
| 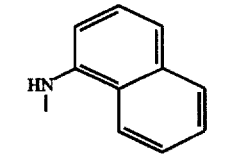 | 0.5 | >100 |
| 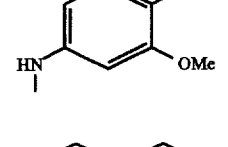 | 50 | >50 |
| 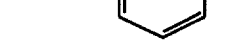 | 10 | >50 |
| 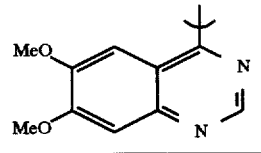 | 2.5 | >50 |
| 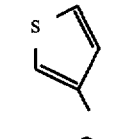 | 10 | >20 |
| 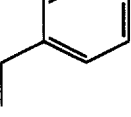 | 20 | ≧20 |

-continued

| Structure | Ick activity IC$_{50}$ (μM) | CSF-R activity IC$_{50}$ (μM) |
|---|---|---|
| 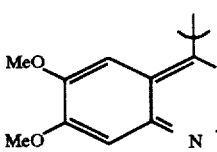 | 1 | >50 |
| 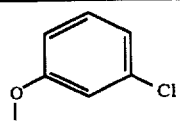 | 2.5 | 3 |
| 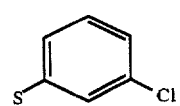 | 5 | 1 |
| 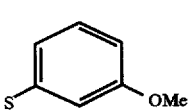 | 5 | >50 |
| 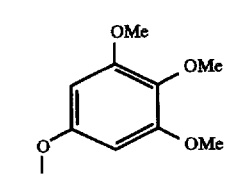 | 2.9 | 15 |

The results obtained by the above experimental methods evidence the useful CSF-1R receptor protein tyrosine kinase inhibition properties of compounds within the scope of the present invention and possess therapeutic value as cellular antiproliferative agents. The above pharmacological test results may be used to determine the dosage and mode of administration for the particular therapy sought.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the for must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization.

Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and if necessary, will be increased by small increments until the optimum effect under the circumstances is reached. The therapeutic human dosage, based on physiological studies using rats, will generally be from about 0.01 mg to about 100 mg/kg of body weight per day or from about 0.4 mg to about 10 g or higher although it may be administered in several different dosage units from once to several times a day. Oral administration requires higher dosages.

We claim:

1. A method for the treatment of inflammation in a patient suffering from such disorder comprising administering to said patient an effective amount of the compound of formula:

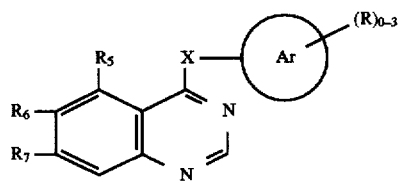

wherein

Ar is a substituted or unsubstituted benzene, pyrrole, thiophene, furan, thiazole, imidazole, pyrazole, 1,2,4-triazole, pyridine, 2(1H)-pyridone, 4(1H)-pyridone, pyrazine, pyrimidine, pyridazine, isothiazole, isoxazole, oxazole, tetrazole, naphthalene, tetralin, naphthyridine, benzofuran, benzothiophene, indole, 2,3-dihydroindole, 1H-indazole, indoline, benzopyrazole, 1,3-benzodioxole, benzoxazole, purine, coumarin, chromone, quinoline, tetrahydroquinoline, isoquinoline, benzimidazole, quinazoline, pyrido[2,3-b]pyrazine, pyrido[3,4-b]pyrazine, pyrido[3,2-c]pyridazine, pyrido[3,4-b]-pyridine, 1 H- pyrazole[3,4-d]pyrimidine, pteridine, 2(1H)-quinolone, 1(2H)-isoquinolone, 1,4-benzisoxazine, benzothiazole, quinoxaline, quinoline-N-oxide, isoquinoline-N-oxide, quinoxaline-N-oxide, quinazoline-N-oxide, benzoxazine, phthalazine, or cinnoline;

X is a bond, O, S, SO, $SO_2$, $OCH_2$, C=C, C≡C, C=S, $SCH_2$, NH, $NHCH_2$, $NR_4$ or $NR_4CH_2$;

R is independently, located at any appropriate position of Ar, hydrogen, alkyl, alkenyl, phenyl, aralkyl, aralkenyl, hydroxy, hydroxyalkyl, alkoxy, alkoxyalkyl, aralkoxy, aryloxy, acyloxy, halo, haloalkyl, nitro, cyano, amino, mono- and di-alkylamino, acylamino, carboxy, carboxyalkyl, carbalkoxy, carbaralkoxy, carbalkoxyalkyl, carbalkoxyalkenyl, aminoalkoxy, amido, mono-alkylamido, di-alkylamido, N, N-cycloalkylamido, sulfonyl, mono-alkyl sulfonyl, di-alkyl sulfonyl, sulfamoyl, mono-alkyl sulfamoyl, di-alkyl sulfamoyl, halophenyl or benzoyl;

$R_4$ is alkyl or benzyl;

$R_5$ is hydrogen, alkyl, alkylthio, cycloalkyl, hydroxy, alkoxy, aralkoxy, aryl, halo, haloalkyl, carboxy or carbalkoxy; and $R_6$ and $R_7$ are alkoxy or aralkoxy; or a pharmaceutically acceptable salt thereof, provided that: when $R_5$ is hydrogen, $R_6$ and $R_7$ are methoxy, and X is a bond, then Ar is other than R substituted phenyl wherein R is hydrogen or (mono- or di-)methoxy; or when $R_5$ is hydrogen, $R_6$ and $R_7$ are alkoxy, X is $NHCH_2$ or $NR_4$, and $R_4$ is hydrogen, then Ar is other than R substituted Ar is phenyl wherein R is hydrogen; or when $R_5$ is hydrogen or methoxy, $R_6$ and $R_7$ are methoxy, and X is $NHCH_2$, then Ar is other than R substituted pyridinyl wherein R is hydrogen, mono-alkyl or mono-hydroxy, or Ar is other than R substituted indol-3-yl wherein R is hydrogen.

* * * * *